United States Patent
Hörlle

(10) Patent No.: US 9,867,649 B2
(45) Date of Patent: Jan. 16, 2018

(54) ELECTROSURGICAL GRIPPING INSTRUMENT

(75) Inventor: Andreas Hörlle, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 14/117,587

(22) PCT Filed: Jul. 18, 2012

(86) PCT No.: PCT/EP2012/064119
§ 371 (c)(1),
(2), (4) Date: Nov. 13, 2013

(87) PCT Pub. No.: WO2013/011070
PCT Pub. Date: Jan. 24, 2013

(65) Prior Publication Data
US 2014/0214030 A1    Jul. 31, 2014

(30) Foreign Application Priority Data
Jul. 20, 2011   (DE) .................. 10 2011 079 494

(51) Int. Cl.
| | |
|---|---|
| *A61B 18/14* | (2006.01) |
| *A61B 18/08* | (2006.01) |
| *A61B 17/00* | (2006.01) |
| *A61B 18/00* | (2006.01) |

(52) U.S. Cl.
CPC ........ *A61B 18/085* (2013.01); *A61B 18/1445* (2013.01); *A61B 2017/00867* (2013.01); *A61B 2018/00607* (2013.01); *A61B 2018/144* (2013.01); *A61B 2018/1452* (2013.01)

(58) Field of Classification Search
CPC .... A61B 2018/1452; A61B 2018/1455; A61B 2018/00601; A61B 17/285; A61B 17/295; A61B 2017/32004; A61B 17/320725; A61B 17/320783
See application file for complete search history.

(56) References Cited

U.S. PATENT DOCUMENTS

| | | | |
|---|---|---|---|
| 2,031,682 A | 2/1936 | Wappler et al. | |
| 3,910,279 A | 10/1975 | Okada et al. | |
| 4,721,117 A * | 1/1988 | Mar ............... | A61M 25/09033 600/585 |
| 4,808,164 A * | 2/1989 | Hess ..................... | A61B 17/22 600/434 |

(Continued)

FOREIGN PATENT DOCUMENTS

| | | |
|---|---|---|
| JP | 2011-179542 A | 9/2011 |
| JP | 49-39797 B2 | 5/2012 |
| JP | 58-46923 B2 | 1/2016 |

OTHER PUBLICATIONS

Search Report issued in German Patent Application No. 10 2011 079 494.8 dated Mar. 14, 2012 (with translation).

(Continued)

*Primary Examiner* — Ronald Hupczey, Jr.
(74) *Attorney, Agent, or Firm* — Oliff PLC

(57) ABSTRACT

The invention relates to an electrosurgical gripping instrument which includes a cutting section for cutting tissue without deformation. The cutting section can be deflected from an idle position for cutting purposes which brings it into contact with the tissue.

17 Claims, 7 Drawing Sheets

(56) References Cited

U.S. PATENT DOCUMENTS

| | | | |
|---|---|---|---|
| 5,415,656 A | 5/1995 | Tihon et al. | |
| 6,190,386 B1 | 2/2001 | Rydell | |
| 8,287,536 B2* | 10/2012 | Mueller et al. | 606/51 |
| 2004/0006340 A1 | 1/2004 | Latterell et al. | |
| 2004/0220564 A1 | 11/2004 | Ho et al. | |
| 2007/0255268 A1* | 11/2007 | Nobis | A61B 18/04 606/32 |
| 2011/0054467 A1 | 3/2011 | Mueller et al. | |
| 2011/0082457 A1* | 4/2011 | Kerr et al. | 606/48 |
| 2012/0041438 A1* | 2/2012 | Nau et al. | 606/45 |
| 2012/0095460 A1* | 4/2012 | Rooks et al. | 606/45 |
| 2013/0338693 A1* | 12/2013 | Kerr et al. | 606/171 |

OTHER PUBLICATIONS

International Search Report issued in International Application No. PCT/EP2012/064119 dated Oct. 17, 2012.

Written Opinion of the International Searching Authority issued in International Application No. PCT/EP2012/064119 dated Oct. 17, 2012.

Translation of Dec. 21, 2015 Office Action issued in Japanese Patent Application No. 2014-520655.

* cited by examiner

ELECTROSURGICAL GRIPPING INSTRUMENT

The invention relates to an electrosurgical gripping instrument. The electrosurgical gripping instrument comprises a first jaw and a second jaw, which are configured to jointly perform a plier-like gripping movement. It further comprises a cutting wire having a cutting section having a first end and a second end, wherein the cutting wire forms a conductive electrode. Further, the electrosurgical gripping instrument comprises a tripping device. The first jaw has a first gripping surface facing the second jaw, and the second jaw has a second gripping surface facing the first jaw.

Electrosurgical gripping instruments as recited supra are used e.g. for transecting tissue. This can be carried out at the same time or temporally offset of a coagulation process. During coagulation, tissue is connected by means of an applied high frequency voltage and a current resulting therefrom, which allows e.g. for closing a blood vessel. During transection, in contrast, tissue is cut through. In an electrosurgical gripping instrument, for transecting and for coagulating, separate electrodes or electrode pairs, respectively.

Document US 2011/005 4467 A1 shows an electrosurgical gripping instrument as recited supra, the cutting wire of which is either attached to a fixed end arranged outside of both jaws or is freely movable between the two jaws. The cutting wire is pushed away from a handle part when the jaws are at least partially closed, so that cutting wire comes into contact with the tissue which is positioned between the jaws. Thereby, the cutting wire is bent such that it forms a loop between the two jaws.

The objective is to provide a simpler design of an electrosurgical gripping instrument.

According to the invention, his is this is achieved by an electrosurgical gripping instrument according to claim 1. Advantageous embodiments can be derived from the dependent claims.

According to the invention, an electrosurgical gripping instrument comprises a first jaw and a second jaw, which are configured such to jointly perform a plier-like gripping movement. The electrosurgical gripping instrument furthermore comprises a cutting wire having a first end and a second end, wherein the second end of the cutting section also forms an end of the cutting wire. The cutting wire forms a conductive electrode. Further, the electrosurgical gripping instrument also comprises an operable tripping device. The first jaw has a first gripping surface facing the second jaw, and the second jaw has a second gripping surface facing the first jaw.

The second end rests on the first jaw. The cutting wire has an idle position, in which the cutting section is arranged on one side of an imaginary plane between the first gripping surface and the second gripping surface, wherein the first jaw is also on the same side. When the tripping device is actuated, the cutting section of the cutting wire bends beyond the plane in lateral direction with reference to its longitudinal axis, transversally to the first gripping surface, towards the second jaw. This lateral bending towards the second jaw is the desired bending direction.

In a simple embodiment, the cutting wire extends in its idle position in an approximately straight line in a groove in the first jaw from its proximal end to the vicinity of the distal end. At its proximal end, the cutting wire continues in one piece and thereby transitions into a pushing device. By placing axial pressure onto the proximal end of the cutting wire, the cutting wire bends out laterally—this leads, in a technical sense, to "bending" (buckling)—and the cutting wire curves out from the recess towards the second jaw, in during operating state, towards the gripped tissue.

In comparison to a state-of-the-art electrosurgical gripping instrument, the electrosurgical gripping instrument according to the invention requires significantly less travel which is necessary for moving the cutting section to completely transect a section of tissue placed between both jaws. This simplifies the configuration of the tripping device for the electronic gripping instrument. Further, the arrangement of the cutting wire according to the invention is significantly more suitable for transecting flat tissue and which, also in contrast to a prior art electrosurgical gripping device, is not deformed during the process of transection.

Typically, the first jaw and the second jaw are hinged by means of a link, for example a swivel joint, a helical joint, a rotational sliding joint or a ball joint. By means of the joint, the jaws can perform a plier-like gripping movement, i.e. the jaws can take a position relative to each other, in which, between their gripping surfaces, a rather large intermediary space is created, into which tissue can be positioned, and the jaws can also be moved towards one another so that the intermediary space is reduced and the tissue positioned there between is gripped.

According to one embodiment, a handle part is connected with the first jaw. Thereby, the second jaw is usually movable relative to the first jaw and the handle component. For that purpose, the second jaw can either be connected with another jaw, so that the plier-like gripping movement can be triggered by pinching the handle part and the additional handle part. Alternatively, however, also a separate control mechanism can be provided, which can move the second jaw relative to the first jaw without the second jaw being connected to another handle part.

The cutting wire is typically a conductive non-insulated wire. By way of example, a metal wire is used. The cutting wire must have a small surface in order that an electric arc can be formed between the cutting wire and a suitable opposite electrode for transecting the tissue. The diameter of the cutting wire is therefore preferably 0.05 to 0.4 mm, particularly preferred between 0.1 mm and 0.2 mm.

According to one embodiment, the electrosurgical gripping instrument comprises a pushing device which, upon actuation of the operable triggering device, exerts a force on the first end of the cutting section, whereby the force has at least has one component in axial direction. In this context, the axial direction is to be understood as a longitudinal direction of the cutting wire directly adjacent to the first end. In contrast, the cutting wire between the first and the second end can already in the idle position be at least partially bent. The force exerted by the pushing device can now act either solely in axial direction or can also have a component perpendicular to the axial direction. In general, the component in axial direction of the cutting section will be the main component, i.e. the greatest force component. The component in axial direction achieves that the cutting section laterally bends out of its idle position. This bending out occurs due to kinking or buckling. In this context, lateral bending out is to be understood as bending out transversal to the longitudinal direction of the cutting wire in direction towards the second jaw. Lateral bending out in the context of this description is linguistically differentiated from sideways bending out of the wire, e.g. transversal to the plane of swiveling of the jaws or of the jaw. In this sense, bending out in sideways direction, as will be described infra, is undesirable and can be prevented e.g. by means of a groove.

The tripping device can be configured for example as a mechanically acting trigger, similar to the trigger of a pistol, at the handle part. Alternatively, for example, a head with mechanical actuation or also an electronic tripping device can be provided. If the electrosurgical gripping instrument has a pushing device, the pushing device will preferably exert a force on the cutting wire when the tripping device is actuated.

According to one embodiment, the pushing device presses the cutting section in direction towards its second end when exerting a force on the cutting wire. This is the case for example when the cutting section is not bent in its idle position and, thus, the axial direction of the cutting wire faces from the first end towards the second end. This provides a particularly simple embodiment.

According to one embodiment, the cutting wire has between the first end of the cutting section and the pushing device a pushing section which transmits the force from the pushing section to the first end. The pushing section can thereby be configured as a section of the cutting wire such that no transition between the pushing section and the cutting section is distinctly visible at the wire. The separation is only provided that the pushing section does not bend out significantly even under pressure, whereas the cutting section bends out for transecting the tissue.

A channel, which is arranged in the electrosurgical gripping instrument between the pushing device and the first jaw, and in which the pushing section extends, serves preferably for the purpose of lateral stabilization of the pushing device. By means of a slightly larger diameter of the channel compared to the diameter of the pushing section of the cutting wire, lateral bending out of the pushing section is prevented, so that the force is transmitted onto the cutting section.

Independent of the presence of a channel, the pushing section can be configured stronger, i.e. less flexible than the cutting section. This is achieved in that the force exerted by the pushing device rather leads to bending out of the cutting section than to bend out of the pushing section.

In an alternative embodiment to the embodiment having a pushing device, the cutting wire consists at least partially of shape-memory material having a phase transformation temperature which is designed such that the cutting section, during heating above the phase transformation temperature, bends out laterally beyond the plane laterally transversal to the first gripping surface towards the second jaw. Preferably, the cutting section is made of said shape memory material. The electrosurgical gripping instrument according to this embodiment preferably has a heating device, which heats the cutting wire above the phase transformation temperature when the operable tripping device is actuated. Thereby, the heating device is preferably an electrical heating instrument.

Preferred shape memory materials are for example alloys made from nickel-titanium (Nitinol), copper-zinc, copper-zinc-aluminum, copper-aluminum-nickel, or iron-nickel-aluminum, or also shape memory polymers. The shape memory material, after being heated above the phase transformation temperature, which for example is at approximately 65° C., takes a predetermined shape. In the case of the cutting section, it is a shape that corresponds to a deflected state of the cutting section. Thereby, typically generate high forces are generated by shape materials. Furthermore, the use of mechanically movable components for triggering the cutting process, as required for the pushing device, can be omitted.

The first gripping surface is that surface of the first jaw which faces towards the second jaw. This does not necessarily mean that each extension of a locally defined surface normal extends through the second jaw or, in other words, that the gripping surface is flat. Rather, the first gripping surface is that surface which, during gripping a tissue by means of the first and the second jaw, comes in contact with that zone of the tissue which is positioned on the side of the first jaw. If the tissue is at least partially flexible, also an uneven first gripping surface can come into complete contact with the tissue. The first gripping surface, however, can also be flat. It is not essential to configure it for shift-free or slip-free gripping of the tissue.

The statements regarding the first gripping surface apply analogously for the second gripping surface at the second jaw.

The second end of the cutting section rests on the jaw. This can for example be realized in that the second end of the cutting wire is arranged adjacent to one end of a groove and is pressed against the end of the groove when a pressure is exerted by the pushing device. Thereby, the second end can be fixated in place. Thereby, the second end is preferably enveloped with a link which stabilizes the cutting wire during deflection from the idle position. For that purpose, the link can have dimensions which support it in its surrounding space such that it at most only can perform small movements in radial direction of the cutting wire. Further, the link is preferably also configured such that the cutting section is imparted with a preferred direction of deflection. For this purpose, the link can receive the cutting section such that a axially imparted force from the cutting section impacts on one side of a pivot point so that the cutting section bends out in direction towards the second jaw.

Alternatively, however, it is for instance also possible to attach the second end at the first jaw, e.g. by means of a hinge, which secures that the cutting wire remains rotatable around the attached second end.

As recited supra, the cutting section, in idle position, is arranged ion one side of an imaginary plane between the first gripping surface and the second gripping surface, whereby also the first jaw is on the same side. The plane is not visible on the gripping instrument and merely serves for delimitation vis-à-vis the prior art. In general, there will be an indefinite number of planes in an electrosurgical gripping instrument according to the invention, wherein the planes are arranged between the first gripping surface and the second gripping surface. It is to be appreciated that this feature of the invention is already realized if there is at least one plane being arranged between the first gripping surface and the second gripping surface, which has the properties that both the cutting section and the first jaw are arranged on one side of the plane.

Bending out in this context is to be understood such that the cutting section bends out at least partially and, therefore, at least partially displaces from the first jaw. The designation "transversal" in this context does not mean vertical but comprises wider, possibly only locally determinable angles of imaginary pathes relative to the gripping surface along which parts of the cutting section move. Thus, also the distance of a respective part of the cutting section of the cutting wire to the second jaw decreases, whereby the cutting section is bent towards the second jaw. Thereby, the cutting wire presses against a tissue being supported between the jaws or is biased towards the tissue.

According to a preferred embodiment, the first jaw furthermore has a groove which is configured in the first gripping surface and which bears the cutting section at least partially in its idle position. For example, the cutting section is completely placed in the groove. In this case, the plane can be positioned at the transitional portion between the groove and the first gripping surface. For example, if the first gripping surface is a flat surface in which the groove is arranged, an imaginary plane in the sense of this invention can be defined by the first gripping surface. Both the first jaw and the cutting section are then positioned in the groove on the same side of the imaginary plane.

According to an alternative embodiment, the cutting section rests in its idle position on the first gripping surface. This can for example be realized in that the first gripping surface is a completely flat surface and the cutting section with its second end is mounted by means of a hinge on the first gripping surface. In comparison to the embodiment having a groove, this yields a simpler manufacture of the electrosurgical gripping instrument.

According to one embodiment, the first end is adjacent to a proximal section of the first jaw. Thus, the tripping device can also be arranged at the proximal end of the first jaw and for example at least partially in a handle part adjacent the first jaw. The second end, in contrast, can be arranged at a distal section of the first jaw, which yields a simple embodiment with a precise cutting effect.

According to a preferred embodiment, the cutting section can bend out far enough to allow that a portion of the cutting section contacts the second gripping surface when the second jaw is in a closed position relative to the first jaw. This secures that the cutting wire is in permanent contact with the tissue and that the tissue can be completely transected.

During operation, the cutting wire is typically connected with an output of a HF (high frequency) generator which supplies HF voltage being suitable for transection.

According to a preferred embodiment, the electrosurgical gripping instrument further comprises a first coagulation section pair with a first lower coagulation section at the first jaw and a first upper coagulation section at the second jaw, and further comprises a second coagulation section pair with a second lower coagulation section at the first jaw and a second upper coagulation section at the second jaw. The cutting section is thereby preferably arranged between the first lower coagulation section and the second lower coagulation section. Such embodiment allows that an instrument can be used both for coagulating and for cutting. If, for example, a blood vessel is positioned between the first jaw and the second jaw of such electrosurgical gripping instrument and a plier-like gripping movement of both jaws is performed so that coagulation sections are adjacent to the blood vessel, the blood vessel can be coagulated on both sides of the cutting wire by means of the coagulation sections. For this purpose, the coagulation electrodes are typically connected with the respective outlets of a HF generator. These shall provide HF voltage such that two respective opposite coagulation sections are oppositely poled so that a respective current flows through the tissue. Thereby, the blood vessel is closed so that after coagulation no more blood can flow out. Subsequently, a high frequency voltage can be applied to the cutting wire and the cutting wire can be deflected from its idle position. Thereby, at the cutting wire an electric arc is formed which transects the tissue. After termination of this process, the blood vessel is transected which prevents further outflow of blood.

The respective coagulation sections can either be configured as individual electrodes, or the two respective lower coagulation sections and/or the two upper coagulation sections can be combined to a single electrode. Such electrode having two coagulation sections can for example be configured U-shaped, whereby respective coagulation sections are configured at respective legs of the U-shape.

Coagulation sections preferably have a significantly larger surface than the cutting wire. Therefore, they can coagulate a larger tissue area and thus provide for sufficiently strong coagulated sections.

According to one embodiment, the electrosurgical gripping instrument further comprises a drain electrode which is arranged at the second jaw, so that it can be touched by the cutting wire when it is deflected from the idle position and the second jaw is in a closed position relative to the first jaw. This drain electrode serves for a counter electrode to the cutting wire, so that the current used for transecting can flow directly through the tissue and does not have to flow through an already coagulated section what can occur when coagulation sections are used as opposite electrodes. Coagulated sections of the tissue have the disadvantage that they are dry and thus have a high electrical resistance. This bears the risk that a large portion of the applied voltage drops over the coagulated section when the current flows between the cutting wire and one of the coagulation sections. Alternatively, however, also at least one of the coagulation sections, if existing, can be used as drain electrode drain. In addition, a drain electrode, arranged externally of the gripping instrument at the patient, can be used.

Additional features and advantages of the invention will become apparent to a person skilled in the art when considering the mentioned embodiments which are now described with reference to the appended Figures, wherein.

Figure 1:
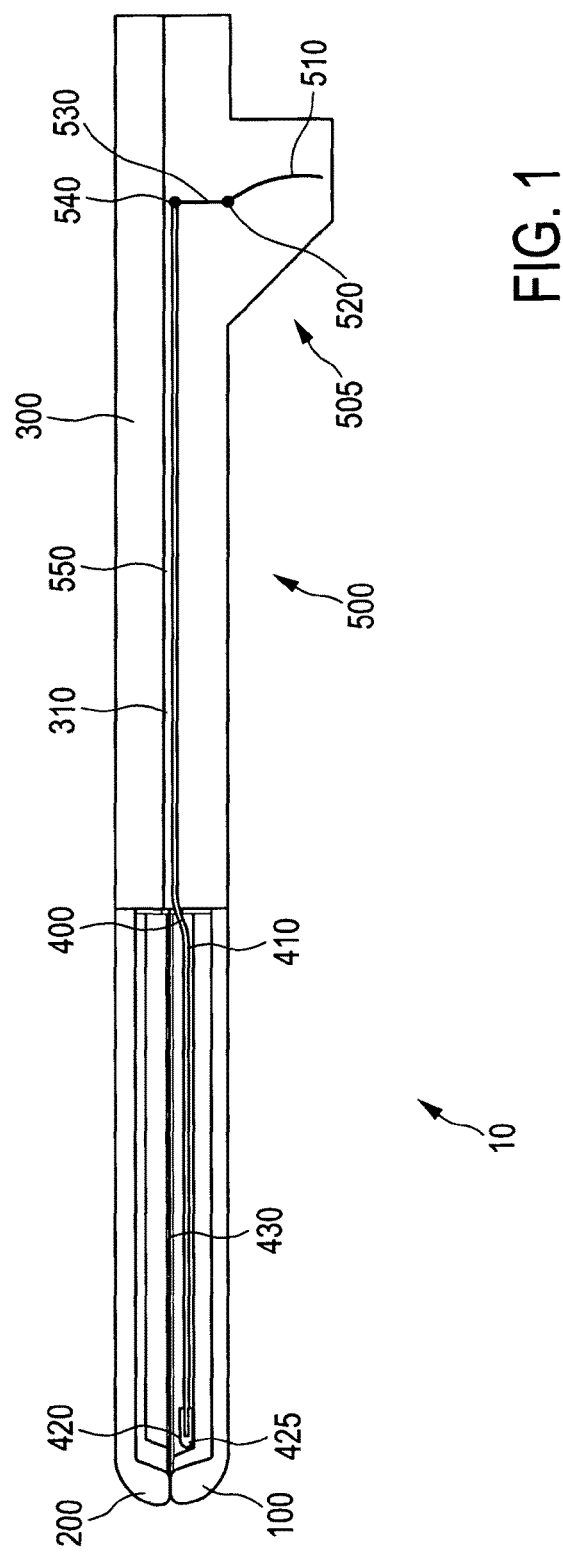
FIG. 1 shows a first embodiment of an electrosurgical gripping instrument according to the invention.

FIG. 1 shows an electrosurgical gripping instrument 10 with a first jaw 100, a second jaw 200 and a handle part 300. The first jaw 100 and the second jaw 200 are in a closed condition. A cutting section 430 of a cutting wire 400 is arranged between the first jaw 100 and the second jaw 200, wherein the cutting section 430 has a first end 410 and a second end 420. The first end 410 is arranged at a proximal section of the first jaw 100, whereas the second end 420 is arranged at a distal section of the first jaw 100. The first end 410 is not characterized by a particular structuring of the cutting wire 400, whereas the second end 420 is also an end of the cutting wire 400.

In the condition shown in FIG. 1, the cutting wire 400 is in idle position. In this idle position, the electrosurgical gripping instrument can be moved towards the tissue to be intersected and grip it.

The electrosurgical gripping instrument 10 further comprises a pushing device 500 which is arranged in the handle part 300. The pushing device 500 can be used with a tripping device 505 that can be operated by a user. The tripping device has a trigger 510, which is mounted to a rotating link

520. The trigger 510 can be moved by the rotating link 520 so that a user can operate the trigger similar to a pistol or a rifle.

A movement of the trigger 510 is transmitted by means of a connecting rod 530 to another rotating link 540, which is connected with a pushing section 550 of the cutting wire 400. The pushing section 550 transitions at the end opposite to the tripping device, which corresponds to the first end 410, transitions into the cutting section 430 arranged between the first end 410 and the second end 420 of the cutting wire 400. Thereby, a movement of the trigger 510 actuated by the user leads in a direction away from the first jaw 100 to a force which is applied at the first end 410 in a direction to the second end 420. Thus, the resulting force also has an axial component with respect to the cutting wire.

The pushing section 550 extends in a channel 310 configured in the handle component 300. The channel 310 has a diameter which encloses the pushing section 550 of the cutting wire 400 so tight that a lateral deflection of the cutting section 550 is possible only to a very limited extent. This allows particular good force transmission from the pushing device 500 to the first end 410 of the cutting section 430.

Figure 2:
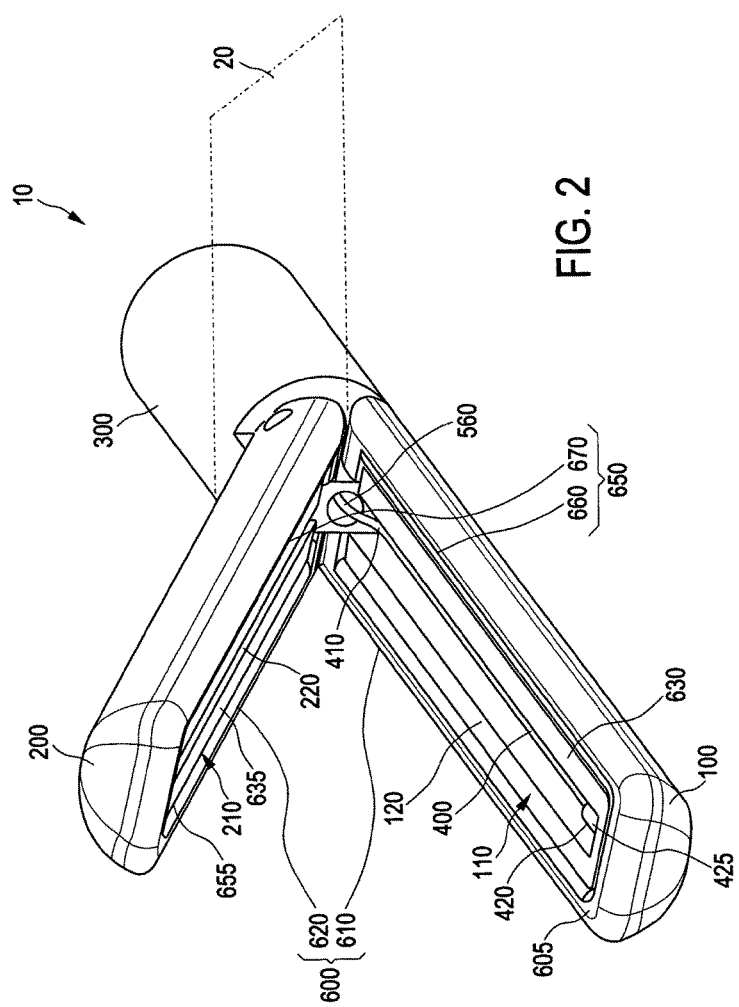
FIG. 2 shows the electrosurgical gripping instrument of FIG. 1 in another view with open jaws.

As apparent from FIG. 2, the electrosurgical gripping instrument 10 has a first gripping surface 110, which faces towards the second jaw 200 and is formed by an insulating recess 630 and a lower coagulation electrode 605 enveloping the insulating recess. Structure and features of the lower coagulation electrode 605 are described infra. The first gripping surface is not a flat surface but structured by the joining of the insulating recess 630 and the lower coagulation electrode 605.

In the insulating recess 630, a slot or a groove 120 is configured which extends from a distal end to a proximal end of the first jaw 100. The groove 120 described here has substantially a square-cut shape. Due to its formation in the insulating recess, the groove is surrounded by the first gripping surface 110 of the first jaw 100.

In the groove 120, the cutting section 430 of the cutting wire 400 is positioned when it is in its non-actuated idle position, as shown in FIGS. 1 and 2. Thus, the cutting section 430 is also completely arranged on one side of a plurality of possible imaginary planes which are arranged between the first gripping surface 110 and a second gripping surface 210 of the second jaw 200, whereby also the first jaw 100 is arranged on the respective same side. Such plane 20 is exemplified.

The slot or groove 120 forms a cannelure for the cutting wire 400 when it bends out towards the second jaw 200 when the tripping device 505 is actuated.

The second end 420 is enveloped by a link 425 which insulates the electrically conductive cutting wire 400 from the first jaw. According to the present embodiment, an insulator is used as a link 425. However, this is nonessential. Rather, also a conductive material can be used if sufficient insulation between the cutting wire 400 and the surrounding electrodes is ensured otherwise. In particular, the link 425 stabilizes the cutting section 430 during lateral bending. For this purpose, in the groove 120 a slot for the link 425 is provided, in which the link is supported. The link 425 further has a dimension which fills most of the available space in the groove 120. Thus, the cutting section 430 can only laterally bend out towards the second jaw 200. In other words, the link 425 acts as a rotating link which allows the cutting wire only one degree of freedom. Lateral bending out to another direction is thus prevented.

The electrosurgical gripping instrument 10 furthermore comprises a first coagulation section pair 600 with a first lower coagulation section 610 and a first upper coagulation section 620 as well as a second coagulation section pair 650 with a second lower coagulation section 660 and a second upper coagulation section 670. The two lower coagulation sections 610, 660 are presently configured as portions of a single lower coagulation electrode 605. Likewise, the two upper coagulation sections 620, 670 are configured as portions of a single upper coagulation electrode 655.

The two coagulation section pairs 600, 650 can be used to coagulate tissue positioned between the first gripping surface 110 and the second gripping surface 210, what for example can be carried out before cutting. The first lower coagulation section 610 and the second lower coagulation section 660 are electrically insulated from the cutting wire 400 by the insulating recess 630.

Further, the electrosurgical gripping instrument 10 comprises another insulating recess 635, which is provided at the second jaw 200 opposite to the insulating recess 630. In the other insulating recess 635, another groove 220 is provided. Thereby, the cutting section 430 is also guided in the area of the second jaw 200 by means of the additional groove 220. Alternatively, according to a non-illustrated embodiment, however, a groove can be omitted at the second jaw. In this case, the second jaw can have a flat insulator as a component of the second gripping surface 210. This flat insulator has the advantage to act as an anvil for the tissue and the cutting wire.

Figure 3:
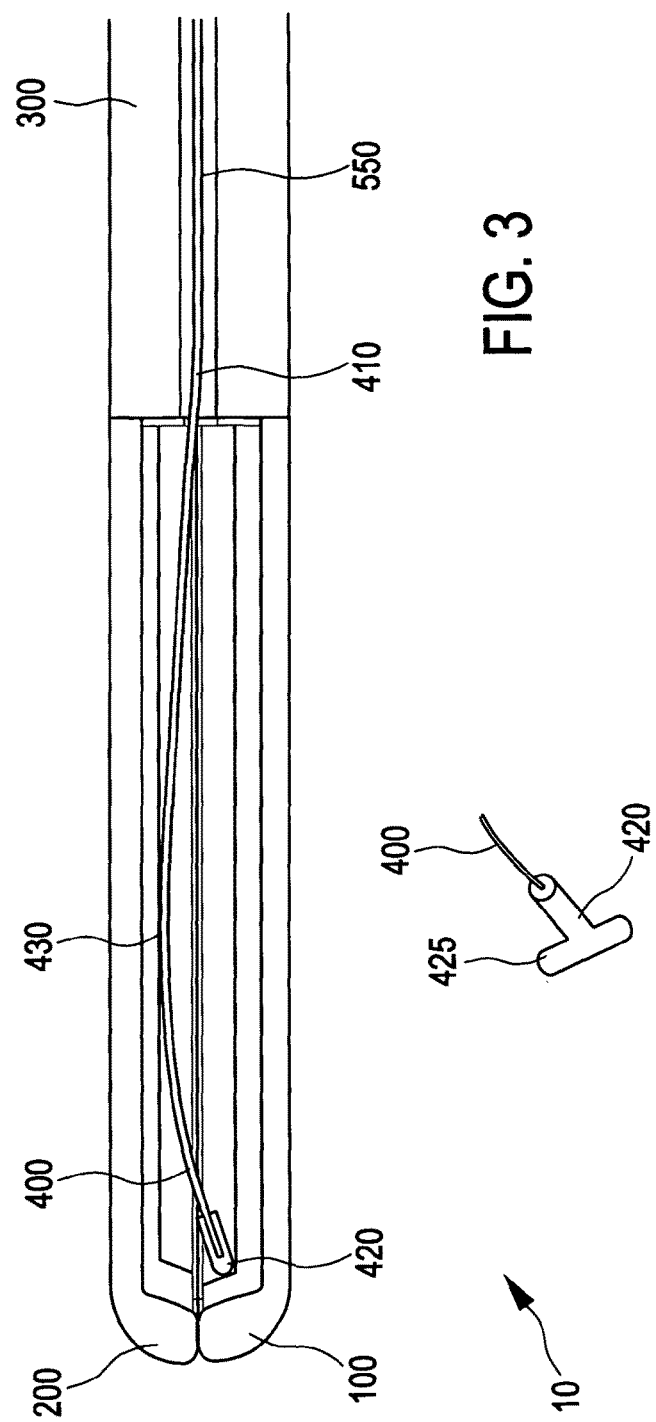
FIG. 3 shows the electrosurgical gripping instrument of FIG. 1 in a sectional view, wherein the cutting wire is in a deflected condition.

FIG. 3 shows the electrosurgical gripping instrument 10 in a sectional view in deflected condition.

As shown in FIG. 3, the cutting wire 400 with its cutting section 430 which is disposed between the first end 410 and the second end 420, is deflected from the idle position. The second end 420 evidently rests on the first jaw 100. The cutting section 430 already abuts the second jaw 200. If tissue would be positioned between the first jaw 100 and the second jaw 200, it could be transected whilst the cutting wire transits from the idle position to the position shown in FIG. 3.

FIG. 3 shows additionally in a separate illustration a perspective view of the second end with the link 425. This clearly demonstrates how the link 425 is laterally fixated in the groove and thus acts as a link.

Figure 4:
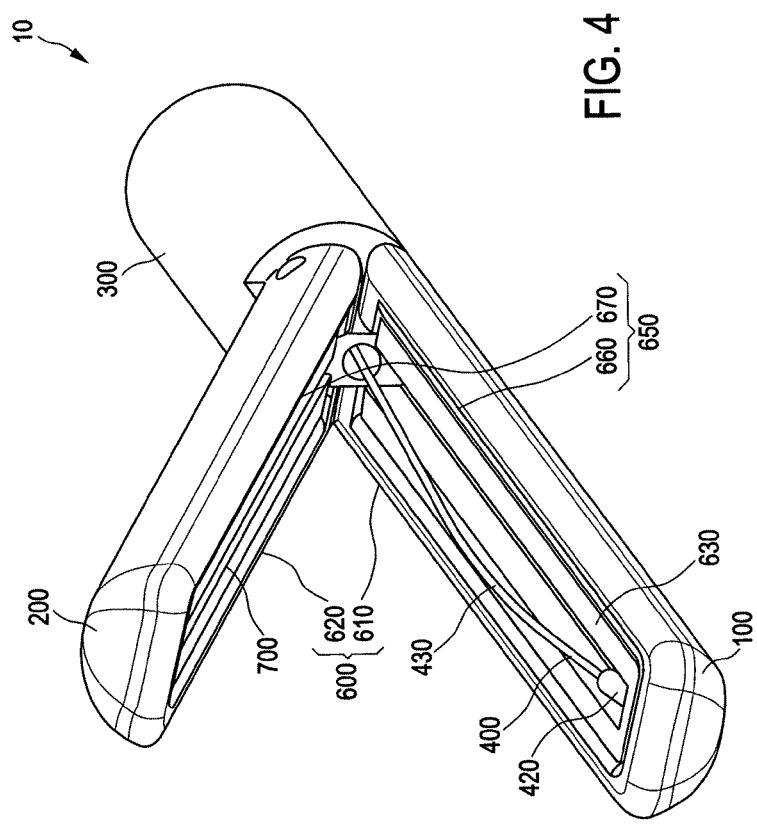
FIG. 4 shows the electrosurgical gripping instrument in the same condition like FIG. 3, however in another view and with open jaws.

FIG. 4 shows the electrosurgical gripping instrument 10 of FIG. 3 with the cutting wire in the same position, however, with open jaws 100, 200.

Figure 5:
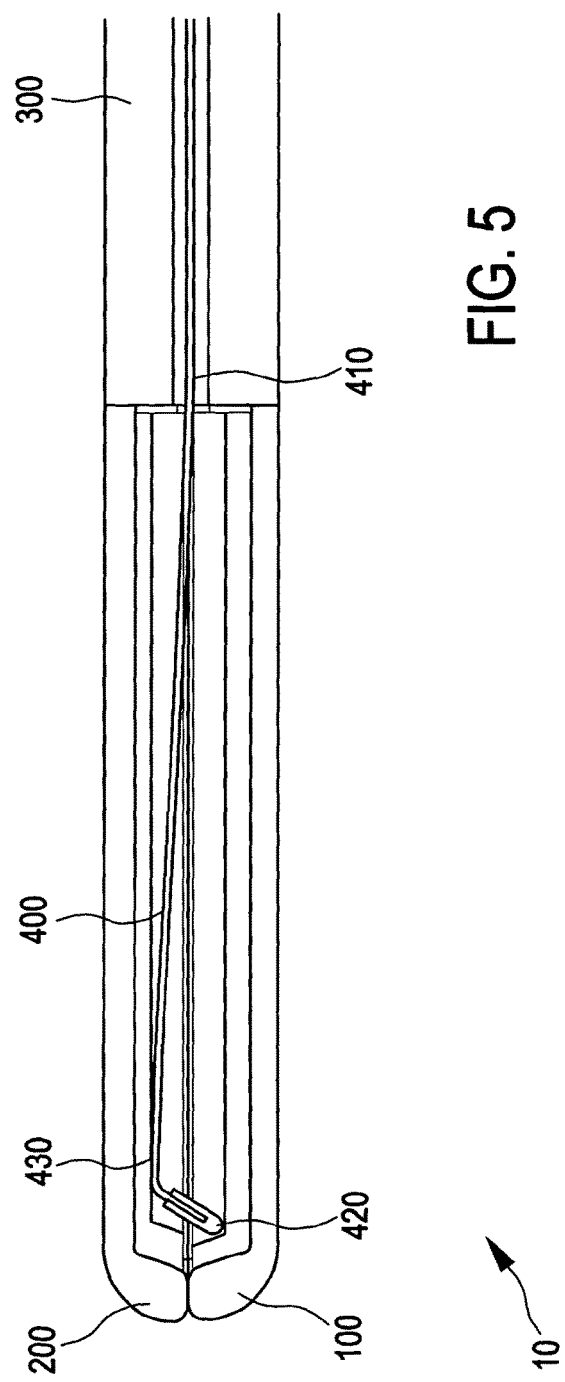
FIG. 5 shows the electrosurgical gripping instrument of FIG. 1, wherein the cutting wire is in a more deflected condition.

FIG. 5 shows the electrosurgical gripping instrument 10, wherein the cutting section 430 is laterally even more deflected from the idle position. Thus, the cutting section 430 is bent out even more than in the condition shown in FIGS. 3 and 4. Also the cutting section 430, as illustrated in FIG. 5, the second jaw 200.

The condition of the cutting section 430 shown in FIG. 5 thus relates to a still later phase of the cutting process than the condition shown in FIG. 3. However, the deflection shown in FIG. 5 highly material-dependent and can also look different.

Figure 6:
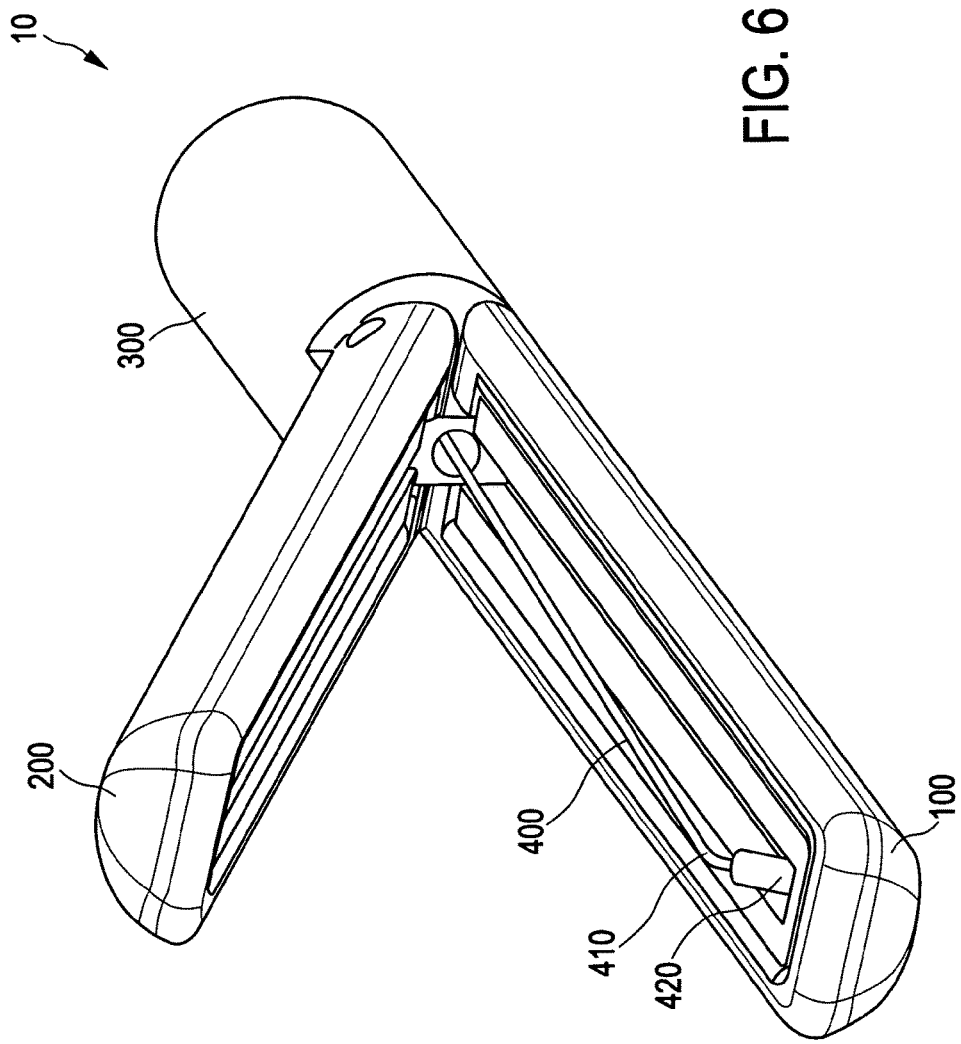
FIG. 6 shows the electrosurgical gripping instrument in the same condition like FIG. 5, however in a different view and with open jaws.

FIG. 6 shows the condition of the electrosurgical gripping instrument 10 according to FIG. 5 with open jaws.

Figure 7:
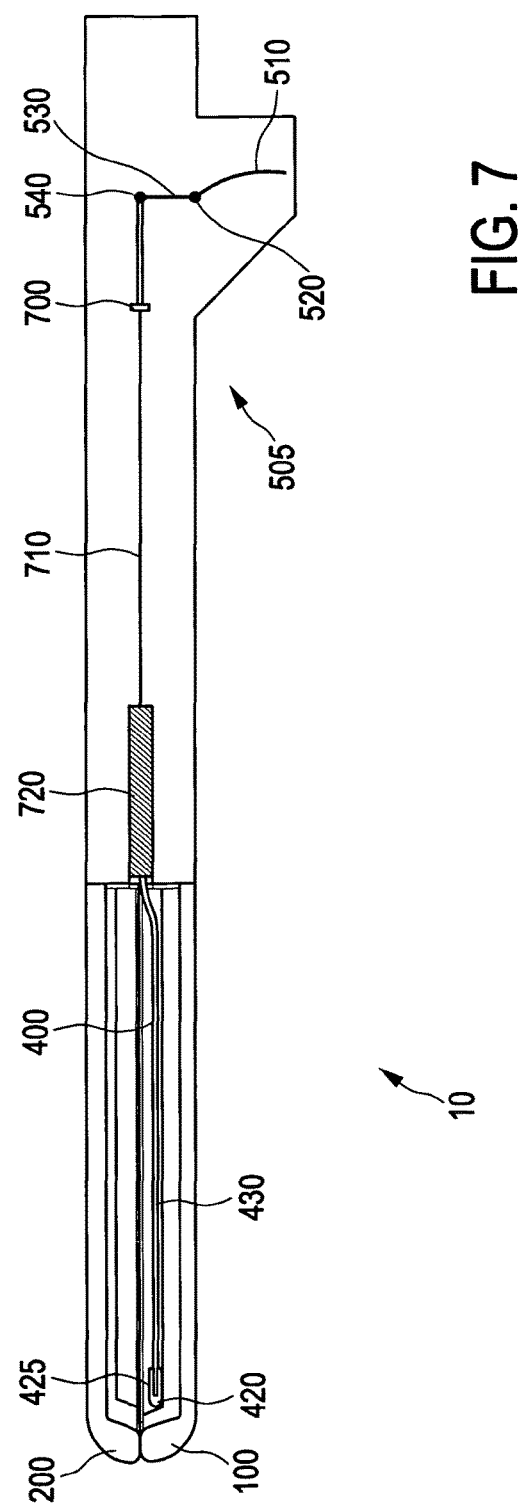
FIG. 7 shows an electrosurgical gripping instrument according to a second embodiment of the invention.

FIG. 7 shows a second embodiment of the invention in which, in contrast to the embodiment shown in FIGS. 1 to 6, the cutting section is not deflected by application of a force. Rather, the cutting wire 430 in the embodiment of FIG. 7 consists of a shape-memory alloy which is designed by means of a respective processing before insertion into the electrosurgical gripping instrument such that it bends out in direction of the second jaw 200 when being heated above its phase transition temperature.

The electrosurgical gripping instrument 10 of FIG. 7 also comprises a tripping device 505 in which, however, a movement of the trigger 510 is no longer transferred directly to the cutting section 430, but is registered by a sensor 700. Subsequently, the sensor 700 activates a heating element 720 by means of a wire 710, which is arranged directly adjacent to the cutting section 430. After activation, the heating element 720 heats the cutting section 430, which thus is heated above its phase transition temperature. This has the effect that the cutting section 430 bends out laterally towards the second jaw 200, similarly like the cutting wire of the first embodiment.

The invention claimed is:

1. An electrosurgical gripping instrument comprising:
a first jaw and a second jaw, which can jointly perform a plier-like gripping movement, wherein the first jaw includes a first gripping surface that faces towards the second jaw and the second jaw includes a second gripping surface that faces towards the first jaw;
a cutting wire that forms a conductive electrode, the cutting wire comprising:
a cutting section with a first end and a second end, wherein the second end of the cutting section defines a distal-most end of the cutting wire and is rotatably fixated at a distal section of the first jaw via a hinge; and
a pushing section;
an operable tripping device; and
a pushing device which, during operation of the tripping device, exerts a pushing force on the first end of the cutting section via the pushing section of the cutting wire, the pushing section being positioned between the first end of the cutting section and the pushing device, whereby the pushing force has at least one component in an axial direction,
wherein:
the cutting wire has an idle position in which the cutting section is arranged on a side of a plane between the first gripping surface and the second gripping surface, wherein the first jaw is on the same side of the plane, and
the cutting section of the cutting wire laterally bends out in a direction transversal to the first gripping surface, and beyond the plane between the two gripping surfaces towards the second jaw when the tripping device is actuated.

2. The electrosurgical gripping instrument according to claim 1, wherein the first jaw further includes a groove which is configured in the first gripping surface and which bears the cutting wire at least partially in its idle position.

3. The electrosurgical gripping instrument according to claim 2, wherein the cutting section in its idle position is completely arranged in the groove.

4. The electrosurgical gripping instrument according to claim 2, wherein the second end of the cutting section is rotatably fixated at a distal end of the groove via the hinge.

5. The electrosurgical gripping instrument according to claim 2, wherein the second end of the cutting section of the cutting wire is enveloped with a link which stabilizes the cutting wire during deflection from the idle position, the link being supported within a slot provided in the groove.

6. The electrosurgical gripping instrument according to claim 1, wherein the cutting section in its idle position contacts the first gripping surface.

7. The electrosurgical gripping instrument according to claim 1, wherein the first end of the cutting section is adjacent to a proximal section of the first jaw.

8. The electrosurgical gripping instrument according to claim 1, further comprising:
a handle part which is connected with the first jaw.

9. The electrosurgical gripping instrument according to claim 1, wherein the second end is enveloped with a link which stabilizes the cutting wire during deflection from the idle position.

10. The electrosurgical gripping instrument according to claim 9, wherein the link insulates the cutting wire from the first jaw.

11. The electrosurgical gripping instrument according to claim 1, wherein the pushing device, when exerting the pushing force upon the first end of the cutting section of the cutting wire, presses the cutting section in a direction towards its second end.

12. The electrosurgical gripping instrument according to claim 1, further comprising, between the pushing device and the first jaw:
a channel in which the pushing section extends and which gives lateral support to the pushing section.

13. The electrosurgical gripping instrument according to claim 1, wherein the cutting section can bend out far enough that a part of the cutting section contacts the second gripping surface when the second jaw is in a closed position relative to the first jaw.

14. The electrosurgical gripping instrument according to claim 1, further comprising:
a lower coagulation electrode at the first jaw and having a first lower coagulation section and a second lower coagulation section between which the cutting section is arranged; and
an upper coagulation electrode at the second jaw.

15. The electrosurgical gripping instrument according to claim 14, wherein the lower coagulation electrode and the upper coagulation electrode are configured in a U-shape and the first lower coagulation section and the second lower coagulation section are respectively configured at legs of the U-shape of the lower coagulation electrode.

16. The electrosurgical gripping instrument according to claim 1, wherein the pushing section of the cutting wire is less flexible than the cutting section of the cutting wire so that the force exerted by the pushing device leads to the bending out of the cutting section.

17. The electrosurgical gripping instrument according to claim 1, wherein the cutting section in its idle position extends in a straight line.

\* \* \* \* \*